United States Patent [19]
Pittrof et al.

[11] Patent Number: 5,747,066
[45] Date of Patent: May 5, 1998

[54] MIXED MICELLES

[75] Inventors: Folker Pittrof, Rheinfelden, Germany; Hans Steffen, Liestal, Switzerland

[73] Assignee: Hoffmann-La Roche Inc., Nutley, N.J.

[21] Appl. No.: 612,047

[22] Filed: Mar. 7, 1996

[30] Foreign Application Priority Data

Mar. 7, 1995 [CH] Switzerland .................. 654/95

[51] Int. Cl.[6] ................... A61K 9/107; A61K 9/127
[52] U.S. Cl. ............... 424/450; 428/402.2; 514/937; 264/4.1
[58] Field of Search ................ 424/450; 264/4.1, 264/4.3; 514/78, 936–943; 428/402.2

[56] References Cited

U.S. PATENT DOCUMENTS

| | | | |
|---|---|---|---|
| 4,158,707 | 6/1979 | Steffen et al. | 424/244 |
| 4,271,196 | 6/1981 | Schmidt | 424/358 |
| 4,694,084 | 9/1987 | Breuninger et al. | 546/25 |

FOREIGN PATENT DOCUMENTS

| | | |
|---|---|---|
| 0 471 309 | 8/1981 | European Pat. Off. . |
| 0 280 887 | 9/1988 | European Pat. Off. . |
| 0 388 817 | 3/1990 | European Pat. Off. . |
| 0 439 042 | 7/1991 | European Pat. Off. . |
| 27 30 570 | 1/1978 | Germany . |
| 90/08534 | 1/1990 | WIPO . |
| 91/07170 | 10/1990 | WIPO . |

OTHER PUBLICATIONS

Colloid Polym. Sci., 269(4):412–414 (1991).
English Abstract of EP-A 0388817 (Document B4) Mar. 1990.
English Abstract of EP-A 0471309 (Document B5) Aug. 1981.
Roseman, et al, Properties Of Sonicated Vesicles Of Three Synthetic Phospholipids, Chemistry and Physics of Lipids, vol. 21, pp. 205–222 (1978).
Szoka, et al, Comparative Properties And Methods Of Preparation of Lipid Vesicles (Liposomes)[1], Ann. Rev. Biophys. vol. 9, pp. 467–508 (1980).
Menger, et al, Chain–Substituted Lipids In Monolayer Films. A Study of Molecular Packing, J. Am. Chem. Soc. vol. 110, pp. 6797–6803 (1988).
Carey, et al, Micelle Formation by Bile Salts, Arch. Intern. Med. vol. 130, pp. 506–527 (1972).
English Abstract of Document B1 Jan. 1978.
English Abstract for Document B2 Sep. 1988.
English Abstract for Document B3 Jul. 1991.

*Primary Examiner*—Gollamudi S. Kishore
*Attorney, Agent, or Firm*—George W. Johnston; Dennis P. Tramaloni; Bruce A. Pokras

[57] ABSTRACT

Mixed micelles for the aqueous solubilization of active substances which are difficultly soluble or insoluble in water with improved storage properties consist of a phosphatide having saturated, branched fatty acid residues and a bile acid salt or dihexanoyllecithin.

44 Claims, No Drawings

MIXED MICELLES

BACKGROUND OF THE INVENTION

The present invention is concerned with novel mixed micelles and compositions which contain such mixed micelles.

Mixed micelles from bile acid salts and natural phosphatides such as egg lecithin or soya lecithin and compositions which contain such mixed micelles are known, e.g., from Patent Publication DE-A-27 30 570. Such micelle systems can be used for the aqueous solubilization of active substances which are difficultly soluble or insoluble in water, e.g., pharmaceutically active substances in parenterally administerable formulations, for improving the parenteral compatibility in the case of water-soluble active substances (see EP-A-0 280 887) or for improving the skin penetration of pharmaceutically active substances or cosmetics (see EP-A-0 439 042). The presence of unsaturated fatty acids in natural phosphatides can lead to peroxide formation which, even with the addition of antioxidants and chelating agents, can adversely affect the stability of oxidation-sensitive active substances which are present in these formulations.

Phosphatides which correspond to the natural phosphatides and which have saturated fatty acid residues would avoid the disadvantage of peroxide formation. However, mixed micelles exist only above a critical temperature, the "phase transition temperature," which in the case of phosphatides with saturated long-chain fatty acid residues lies substantially higher than room temperature. For example, in the case of soya lecithin the transition temperature is about 50° C. for fully hydrogenated soya lecithin in contrast to about −18° C. for the non-hydrogenated product. This circumstance is an obstacle to the use, e.g., of perhydrogenated soya lecithin for the production of mixed micelles for storage temperatures of room temperature or thereunder.

Lecithins with short-chain carboxylic acids (<C8) have a low phase transition temperature, so that in principle mixed micelles containing such lecithins can be produced at room temperature. These lecithins are, however, too toxic or hemolytic to be used parenterally. Mixed micelles from dihexanoyllecithin and egg lecithin or soya lecithin have been proposed for such applications (see EP-A-0 011 745).

Dilaurylphosphatidylcholine (DLPC) exhibits a phase transition temperature of about 0° C. and has no hemolytic activity itself. However, it lacks the antihemolytic effect which is typical of egg lecithin and soya lecithin and which is important for use in bile salt mixed micelles, and thus DLPC-bile salt mixed micelles can likewise not be used parenterally.

SUMMARY OF THE INVENTION

It has now surprisingly been found that mixed micelles are formed in the region of normal (room) temperature or thereunder with phosphatides which contain saturated fatty acid residues when at least one of the fatty acid residues is branched, i.e., when a straight chain fatty acid is substituted at from one to three carbon atoms by $C_{1-5}$-alkyl, (hereinafter also referred to as isophosphatides or isolecithins).

DETAILED DESCRIPTION OF THE INVENTION

The invention accordingly directed to fluid mixed micelle compositions containing micelles dispersed in an aqueous media wherein the micelles comprise:

a) a first compound which is a phosphatide in which two of the hydroxyl groups of the glycerol moiety of said phosphatide are esterified with:

residues formed from saturated fatty acids which independently contain a straight chain of from 14 to 20 carbon atoms and one or both of said fatty acids is substituted at one to three carbon atoms with $C_{1-5}$-alkyl, and b) a second compound which is a bile acid salt or dihexanoyllecithin, wherein the concentration of the first compound in said composition is in the range from about 1 mg/ml to about 200 mg/ml and the molar ratio of the first compound to the second compound in said composition is in the range from 0.1:1 to 2:1;

or a lyophilizate of said composition.

The first compound is preferably a phosphatide which has the described fatty acid residues, at least one of which is substituted as described. The second micelle forming compound is preferably a bile acid salt.

The mixed micelle compositions of the invention may be used, per se, as topical skin smoothing compositions. However, the preferred mixed micelle compositions of the invention further comprise a pharmaceutically active compound dispersed therein. For the purposes of this invention, compounds having purely cosmetic indications are considered to be within the term "pharmaceutically active."

The invention is also directed to the use of such mixed miscelles for the aqueous solubilization of active substances which are difficultly soluble or insoluble in water, e.g., pharmaceutically active substances in parenterally administerable formulations, for improving the parenteral compatibility of water-soluble active substances, or for improving the skin penetration of pharmaceutically active substances, including cosmetics. Additionally, the invention is directed to the use of the mixed micelles of the invention in diagnostics for the stabilization of proteins, such as membrane-bound receptors.

The fatty acid residues of the phosphatides useful in accordance with the invention—are preferably singly substituted by a methyl or ethyl group, at one or, preferably both, of the fatty acid residues. Fatty acid residues which are substituted in the middle part of the chain, i.e., in positions 8, 10 or 12, are preferred.

Furthermore, phosphatides which contain fatty acid residues having an odd number of carbon atoms in the straight chain are preferred. The 10-methylnonadecanoyl, the 10-methylstearoyl, the 8-methylheptadecanoyl, the 8-methylpalmitoyl and the 10-ethylstearoyl residues are examples of saturated, substituted fatty acid residues of isophosphatides which are useful in accordance with the invention. Examples of isophosphatides which can be used in accordance with the invention are:

1,2-di(10-methylnonadecanoyl)-sn-glycero-3-phosphocholine, 1,2-di(10-methylstearoyl)-sn-glycero-3-phosphocholine, 1,2-di(8-methylheptadecanoyl)-sn-glycero-3-phosphocholine, 1,2-di(8-methylpalmitoyl)-sn-glycero-3-phosphocholine, and 1,2-di(10-ethylstearoyl)-sn-glycero-3-phosphocholine, as well as enantiomers thereof. Further examples of phosphatides in accordance with the invention are the phosphatidylethanolamines having saturated, substituted fatty acid residues which correspond to the above phosphocholines:

1,2-di(10-methylnonadecanoyl)-sn-glycero-3-phosphoethanolamine, 1,2-di(10-methylstearoyl)-sn-glycero-3-phosphoethanolamine, 1,2-di(8-methylheptadecanoyl)-sn-glycero-3-phosphoethanolamine, 1,2-di(8-methylpalmitoyl)-sn-glycero-3-phosphoethanolamine, and 1,2-di(10-ethylstearoyl)-sn-glycero-3-phosphoethanolamine.

The most preferred phosphatide for use in accordance with the invention is 1,2-di(10-methylnonadecanoyl)-sn-glycero-3-phosphocholine, with which mixed micelles can also be formed under refrigeration conditions.

The mixed micelles in accordance with the invention can be manufactured in aqueous solution from the components, i.e., from a bile acid salt or dihexanoyllecithin and the phosphatides described herein, by any conventional means. Examples of such conventional methods are described in Patent Publications DE-A-27 30 570 and WO 90/08534. For example, mixed micelles of the invention may be prepared by dissolving the components, either individually or as a mixture and an active substance (which is optionally added) in an organic solvent, e.g., methylene chloride, ethanol and/or methanol, removing the solvent, preferably on a rotary evaporator, and dissolving the residue in water or an aqueous solution of pharmaceutical adjuvants, such as buffers or isotonizing agents. The mixed micelles of the invention may also be prepared by suspending the free bile acids in water, optionally with the addition of pharmaceutical adjuvants and/or water-soluble active substances, dispersing the phosphatide and optionally active substances in the suspension and neutralizing the suspension with a base, e.g., an alkali hydroxide.

Mixed micelles which contain a bile acid salt are preferred. The bile acid salt is not critical, so any conventional bile acid salts which are used in the preparation of mixed micelles may be used in accordance with the invention. Examples of bile acid salts which come into consideration for the mixed micelles in accordance with the invention are alkali salts, such as sodium salts, of cholic acid, glycocholic acid, taurocholic acid, deoxycholic acid, glyco- or taurodeoxycholic acid, chenodeoxycholic acid and glyco- or taurochenoxydeoxycholic acid. Sodium glycocholate is preferred.

In aqueous solutions, the phosphatide component of the mixed micelles of the invention can be present in a concentration in the range from about 1 mg/ml to about 200 mg/ml. Preferably, the phosphatide is present in a concentration in the range from about 10 mg/ml to about 200 mg/ml. The phosphatide:bile acid salt molar ratio is in the range from about 0.1:1 to about 2:1, preferably 0.8:1 to 1.5:1. The bile acid salt concentration should, however, always lie above the bile salt-specific critical micelle formation concentration (CMC). The CMC of a bile acid salt may be determined by any conventional means (D. J. Cabral and D. N. Small in: Handbook of Physiology, The Gastrointestinal System III Chapter 31: Physical Chemistry of Bile; )

Mixed micelles from 1,2-di(10-methylnonadecanoyl)-sn-glycero-3-phosphocholine and sodium glycholate are especially preferred.

If desired, the mixed micelles in accordance with the invention can contain pharmaceutically active substances for parenteral, topical (including cosmetics) or oral administration, especially active substances which are insoluble or difficultly soluble in water, as well as adjuvants, such as buffers, e.g., phosphate, citrate or Tris buffer; or isotonizing agents, e.g., sodium chloride, mannitol, sorbitol or glucose; or preservatives, e.g. methyl or propyl p-hydroxybenzoate, benzyl alcohol or phenol. Examples of pharmaceutically active substances which can be present in the mixed micelles in accordance with the invention are retinoids such as all-trans, 13-cis and 9-cis retinoic acid and their derivatives including aromatic compounds such as etretinate; vitamin K, vitamin D and their derivatives; peroxide-containing active substances such as artemisinin, arteflene and benzoyl peroxide; water-soluble low-molecular and high-molecular active substances such as, e.g., pyrimidine analogues (5-fluorouracil); heparin; and proteins.

Examples of proteins useful in accordance with the invention are interferons (IFN), such as IFN-α, IFN-β, IFN-γ; hybrid interferons; interleukins (IL), such as IL-1 (ETAF, LAF), IL-2 (TCGF), IL-3 (multi-CSF, MCGF), IL-4 (BSF-1, BCGF-2), IL-5 (TRF, BCGF-II), IL-7 (lymphopoietin 1); lymphotoxin (TNF-β); macrophage inhibitory factor (MIF); thymopoietin (TPO); transforming growth factor-α (TGF-α); transforming growth factor-β(TGF-β); tumour necrosis factor (TNF-α, cachectin, DIF); uromodulin (Tamm-Horsfall protein); neuroleukin; CD4); granulocyte colony stimulating factor (G-CSF), granulocyte-macrophage colony stimulating factor (GM-CSF, CSF-2), macrophage colony stimulating factor (CSF-1, M-CSF); antibody or antibody-drug conjugates, hybrid proteins such as IL-2 diphtheria toxin and proteins for the preparation of vaccines against AIDS, malaria, hepatitis, herpes, influenza, poliomyelitis and other infectious diseases.

Examples of compounds having cosmetics indications which can be present in the mixed micelles in accordance with the invention are vitamin E, panthenol and moisturizers such as lactic acid and pyrrolidonecarboxylic acid and their salts.

The mixed micelle in accordance with the invention can be prepared as compositions in aqueous or organic-aqueous media or as lyophilizates of such compositions.

The mixed micelle compositions of the invention may contain one or more pharmaceutically active compounds. The concentration of a pharmaceutically active compound in the mixed micelle compositions of the invention is not critical to the present invention, but simply should be sufficient to treat the disease or condition for which the active compound is indicated. The maximum amount of water—insoluble or difficult soluble pharmaceutically active compound that may be present in the mixed micelle compositions of the invention depends upon the capacity of the mixed micelles to solubilize the particular active compound. Generally, the mixed micelle solutions can contain pharmaceutically active substances in amounts up to about 20 mg/ml.

Phosphatides having the above-described substituted fatty acid residues are generally known. They are present, e.g., in mother's milk and in skin lipids. They can be prepared, e.g., by partially esterifying glycerol with the corresponding saturated, substituted fatty acids to give the di-ester, phosphorylating the di-ester and reacting with a suitable choline salt, such as choline tosylate, as described hereinafter or in analogy thereto.

The invention is illustrated in more detail by the following Examples.

EXAMPLE 1

Preparation of 1,2-di(10-methylnonadecanoyl)-sn-glycero-3-phosphocholine:

a) 59.8 g of dicyclohexylcarbodiimide and 35.4 g of 4-dimethylamino-pyridine were added while stirring to a solution of 90.2 g of 10-methyl-nonadecanoic acid (70%)

and 21.0 g of (R)-benzyloxy-1,2-propanediol in 2 l of methylene chloride. Then, the mixture was stirred at room temperature for 24 hours. The separated urea was filtered off, rinsed three times with 200 ml of n-hexane each time and the combined filtrates were concentrated at 35° C. in a water-jet vacuum. The crude product was treated with 500 ml of n-hexane, warmed to 40° C. while stirring and thereafter cooled to 0°–5° C., likewise while stirring. The separated urea was rinsed with 250 ml of n-hexane and the filtrate was evaporated at 35° C. in a water-jet vacuum. The residue was dissolved in 210 ml of n-hexane and chromatographed with about 23 l of n-hexane/ethyl acetate (95:5) on 2.5 kg of silica gel in 10.5 l of n-hexane. The product-containing fractions were combined, concentrated, dissolved in 100 ml of toluene and purified over 4 kg of silica gel firstly with about 35 l of toluene and then with about 15 l of n-hexane/ethyl acetate (95:5). The fractions which were uniform according to chromatography were combined and concentrated at 40° C. on a rotary evaporator in a water-jet vacuum.

b) 56.5 g of the diester obtained in a) were dissolved in 2 l of ethyl acetate, treated with 5.6 g of 5% palladium/carbon and hydrogenated at room temperature overnight. The reaction mixture was filtered over 300 g of sodium sulphate and rinsed with 1.5 l of ethyl acetate. The combined ethyl acetate phases were concentrated at 40° C. in a water-jet vacuum. A light yellowish oil was obtained.

c) 20 g of the oil obtained in b) were dissolved in 280 ml of chloroform at room temperature under argon and while stirring. Thereafter, at this temperature while stirring there were added 4 ml (43.6 mmol) of phosphorus oxychloride and 2 minutes later 5.2 ml (43.6 mmol) of quinoline. The reaction mixture was stirred at 30° C. for 2 hours, thereafter cooled to room temperature and then treated firstly with 17.8 g of quinoline tosylate and then with 16.8 ml of pyridine. The reaction mixture was stirred at room temperature overnight (16–18 hours). 44 ml of deionized water were then added dropwise to the reaction mixture within 5 minutes while stirring and the mixture was subsequently treated with 11.5 g of sodium hydrogen carbonate and stirred for 30 minutes. The reaction mixture was treated with 250 ml of chloroform and 100 ml of methanol and shaken vigorously, and the organic phase was separated and washed in succession with 260 ml of deionized water/methanol (8:5), 290 ml of 1N hydrochloric acid/methanol (16:13), 320 ml of deionized water/methanol (1:1) and 320 ml of deionized water/methanol (1:1). The aqueous phases were back-washed in succession with 100 ml of chloroform. The combined chloroform phases were dried over sodium sulphate and concentrated in a water-jet vacuum at 40° C. The residual oil was taken up in 300 ml of methanol, stirred at 30°–35° C. for 10 minutes and then cooled to 0° C. and stirred at this temperature for 1 hour. After standing in an ice bath for 20 minutes the deposited oil was separated. The clear filtrate was cooled to −5° C., left at this temperature for 10 minutes and the deposited oil was again separated. The supernatant was concentrated at 40° C. in a water-jet vacuum. The residue was dissolved in 100 ml of diethyl ether and treated with 150 ml of acetone while stirring, the ether was removed at 35° C. and the oil was dissolved in 130ml of diethyl ether and treated with 120 ml of acetone. After removing the ether at 35° C. the residue was treated with 50 ml of acetone, cooled to 18° C. and decanted off from deposited oil. The thus-obtained oily 1,2-di(10-methylnonadecanoyl)-sn-glycero-3-phosphocholine was dried at room temperature in a vacuum at 1 mbar.

EXAMPLE 2

Manufacture of a mixed micelle solution:

A mixed micelle solution was manufactured from a stock solution of 20 ml of 0.1M 1,2-di(10-methylnonadecanoyl)-sn-glycero-3-phosphocholine in methylene chloride and 20 ml of 0.1M Na glycocholate in methanol by evaporating the solvent and taking up the residue, which remained behind as a film, in 2 ml of demineralized water.

EXAMPLE 3

Mixed micelle solutions (conventional and in accordance with the invention) of the following compositions were manufactured:

|  | /01 | /02 | /03 | /04 | /05 |
|---|---|---|---|---|---|
| 9-cis-Retinoic acid | 0.5 | 0.5 | 0.5 | 0.5 | 0.5 mg |
| Ethanol 94% (w/w) | 100.0 | 100.0 | 100.0 | 100.0 | 100.0 mg |
| Glycocholic acid | 88.5 | 88.5 | 88.5 | 88.5 | 88.5 mg |
| Iso-lecithin* | 163 | 163 |  |  | mg |
| Soya-lecithin** |  |  | 152 | 152 | 152 mg |
| NaOH ad | pH 6.0 | pH 6.0 | pH 6.0 | pH 6.0 | pH 6.0 |
| Benzyl alcohol | 10.0 | 10.0 | 10.0 | 10.0 | 10.0 mg |
| dl-α-Tocopherol | — | 10.0 | — | 10.0 | 10.0 μg |
| Ascorbic acid | — | 50.0 | — | — | 50.0 μg |
| Water ad | 1.0 | 1.0 | 1.0 | 1.0 | 1.0 ml |

*1,2-Di-(10-methylnonadecanoyl)-sn-glycero-3-phosphocholine (in accordance with the invention)
**Conventional For the manufacture of the solutions, ethanol and water were degassed and all manipulations were performed under red light and nitrogen. The water-soluble excipients were dissolved in water and the pH was adjusted to 6.0. 9-cis-Retinoic acid and tocopherol were dissolved in ethanol. The solution of the water-soluble substances was added to the ethanolic lecithin solution and stirred until a clear solution had formed (18 hours). Thereafter, the ethanolic 9-cis-retinoic acid solution was added and the volume was adjusted. The thus-obtained mixed micelle solution was filled into vials having Teflon stoppers and sterilized at 120° C. for 20 minutes.

The data in Table 1 demonstrate the chemical stability of the 9-cis retinoic acid in in a composition of the invention after storage for 3 months at various temperatures. The results show that in the mixed micelled compositions in accordance with the invention (composition /01–/02), in contrast to conventional solutions (composition /03–/05), no oxidative degradation of the 9-cis-retinoic acid occurred. The loss of 9-cis-retinoic acid in the mixed micelled compositions in accordance with the invention after sterilization is not due to oxidative degradation, but to an increased isomerization.

Furthermore, the mixed micelles in accordance with the invention, are comparable in their haemolytic and, respectively, antihaemolytic activity with conventional mixed micelle compositions.

TABLE 1

Chemical stability of 9-cis-retinoic acid in mixed micelles

| Storage time (months) | Antioxidant | Treatment | Mixed micelles in accordance with the invention 9-cis- | | | Conventional mixed micelles 9-cis- | | |
| --- | --- | --- | --- | --- | --- | --- | --- | --- |
| | | | Retinoic acid % | Isomers % | Total % | Retinoic acid % | Isomers % | Total % |
| initial | none | — | 99.4 | 3.33 | 102.73 | 87.6 | 0.48 | 88.08 |
| | none | ster. | 25.0 | 75.4 | 100.4 | 74.6 | 1.44 | 76.04 |
| | toc. + asc. | — | 99.2 | 3.6 | 102.8 | 94.0 | 0.50 | 94.5 |
| | toc. + asc. | ster. | 52.0 | 49.0 | 101 | 87.0 | 1.20 | 88.2 |
| | toc. | — | | | | 95.0 | 0.06 | 95.06 |
| | toc. | ster. | | | | 76.0 | 2.06 | 78.06 |
| 3 −20° C. | none | — | 95.4 | 3.4 | 98.8 | 84.0 | 0.70 | 84.7 |
| | none | ster. | | | | | | |
| | toc. + asc. | — | 94.0 | 3.6 | 97.6 | 93.6 | 0.05 | 93.65 |
| | toc. + asc. | ster. | | | | 86.6 | 0.60 | 87.2 |
| | toc. | — | | | | | | |
| | toc. | ster. | | | | | | |
| 3 5° C. | none | — | 95.0 | 4.2 | 99.2 | 68.6 | 0.90 | 69.5 |
| | none | ster. | 24.8 | 75.5 | 100.3 | 66.0 | 1.90 | 67.9 |
| | toc. + asc. | — | 94.4 | 4.2 | 98.6 | 91.6 | 0.06 | 91.66 |
| | toc. + asc. | ster. | 49.0 | 50.8 | 99.8 | 73.8 | 1.20 | 75 |
| | toc. | — | | | | 82.0 | 0.50 | 82.5 |
| | toc. | ster. | | | | 70.2 | 1.80 | 72 |
| 3 25° C. | none | — | 87.0 | 12.3 | 99.3 | 34.4 | 2.10 | 36.5 |
| | none | ser. | 24.4 | 75.3 | 99.7 | 55.8 | 1.90 | 57.7 |
| | toc. + asc. | — | 77.6 | 20.6 | 98.2 | 63.0 | 0.80 | 63.8 |
| | toc. + asc. | ster. | 46.8 | 52.6 | 99.4 | 47.9 | 1.20 | 49 |
| | toc. | — | | | | 58.8 | 2.10 | 60.9 |
| | toc. | ster. | | | | 67.2 | 2.10 | 69.3 |
| 3 40° C. | none | — | 64.4 | 30.7 | 95.1 | 43.4 | 2.40 | 45.8 |
| | none | ster. | 22.4 | 75.3 | 97.7 | 58.6 | 2.10 | 60.7 |
| | toc. + asc. | — | 34.4 | 64.0 | 98.4 | 11.2 | 2.20 | 13.4 |
| | toc. + asc. | ster. | 30.0 | 68.1 | 98.i | 16.2 | 2.60 | 18.8 |
| | toc. | — | | | | 66.6 | 1.60 | 68.2 |
| | toc. | ster. | | | | 73.8 | 2.00 | 75.8 | toc: Tocopherol
asc: Ascorbic acid
ster: Sterilization

We claim:

1. A fluid mixed micelle composition containing micelles dispersed in an aqueous media wherein said micelles comprise:
   a) a first compound which is a phosphatide in which two of the hydroxyl groups of the glycerol moiety of said phosphatide are esterified with:
      residues formed from saturated fatty acids which independently contain a straight chain of from 14 to 20 carbon atoms and one or both of said fatty acids is substituted at one to three carbon atoms with $C_{1-5}$-alkyl, and
   b) a second compound which is a bile acid salt or dihexanoyllecithin,
wherein the concentration of the first compound in said composition is in the range from about 1 mg/ml to about 200 mg/ml and the molar ratio of the first compound to the second compound in said composition is in the range from 0.1:1 to 2:1;
or a lyophilozate of said composition.

2. The mixed micelle composition of claim 1 wherein the first compound is a phosphatide in which two of the hydroxyl groups of the glycerol moiety of said phosphatide are esterified with said fatty acid residues, and the second compound is a bile acid salt.

3. The mixed micelle composition of claim 2 wherein the fatty acid residues of said phosphatide are the same and have an odd number of carbon atoms in a straight chain.

4. The mixed micelle composition of claim 3 wherein the fatty acid residues of said phosphatide are singly substituted by a methyl or ethyl group.

5. The mixed micelle composition of claim 4 wherein the fatty acid residues of said phosphatide are substituted at carbon 8, 10 or 12 of said fatty acid residues.

6. The mixed micelle composition of claim 5 wherein the concentration of said phosphatide is in the range from 10 mg/ml to 200 mg/ml, and the molar ratio of said phosphatide to said bile acid salt is in the range from 0.8:1 to 1.5:1.

7. The mixed micelle composition of claim 6 wherein said micelles further comprise a pharmaceutically active compound and said pharmaceutically active compound is present in said composition in a pharamaceutically effective concentration up to 50 mg/ml.

8. The mixed micelle composition of claim 7 wherein said phosphatide is 1,2-di(10-methylnonadecanoyl)-sn-glycero-3-phosphocholine its enantiomers and its corresponding phosphoethanolamines.

9. The mixed micelle composition of claim 8 wherein said phosphatide is 1,2-di(10-methylnonadecanoyl)-sn-glycero-3-phosphocholine.

10. The mixed micelle composition of claim 9 wherein said bile acid salt is sodium glycocholate.

11. The mixed micelle composition of claim 7 wherein said phosphatide is 1,2-di(10-methylstearoyl)-sn-glycero-3-phosphocholine, its enantiomers and its corresponding phosphoethanolamines.

12. The mixed micelle composition of claim 11 wherein said phosphatide is 1,2-di(10-methylstearoyl)-sn-glycero-3-phosphocholine.

13. The mixed micelle composition of claim 12 wherein said bile acid salt is sodium glycocholate.

14. The mixed micelle composition of claim 7 wherein said phosphatide is 1,2-di(8-methylheptadecanoyl)-sn-glycero-3-phosphocholine, its enantiomers and its corresponding phosphoethanolamines.

15. The mixed micelle composition of claim 14 wherein said phosphatide is 1,2-di(8-methylheptadecanoyl)-sn-glycero-3-phosphocholine.

16. The mixed micelle composition of claim 15 wherein said bile acid salt is sodium glycocholate.

17. The mixed micelle composition of claim 7 wherein said phosphatide is 1,2-di(8-methylpalmitoyl)-sn-glycero-3-phosphocholine, its enantiomers and its corresponding phosphoethanolamines.

18. The mixed micelle composition of claim 17 wherein said phosphatide is 1,2-di(8-methylpalmitoyl)-sn-glycero-3-phosphocholine.

19. The mixed micelle composition of claim 18 wherein said bile acid salt is sodium glycocholate.

20. The mixed micelle composition of claim 7 wherein said phosphatide is 1,2-di(10-ethylstearoyl)-sn-glycero-3-phosphocholine, its enantiomers and its corresponding phosphoethanolamines.

21. The mixed micelle composition of claim 20 wherein said phosphatide is 1,2-di(10-ethylstearoyl)-sn-glycero-3-phosphocholine.

22. The mixed micelle composition of claim 21 wherein said bile acid salt is sodium glycocholate.

23. A method of making a mixed micelle composition comprising dissolving in an aqueous media:

a) a first compound which is a phosphatide in which two of the hydroxyl groups of the glycerol moiety of said phosphatide are esterified with: residues formed from saturated fatty acids which independently contain a straight chain of from 14 to 20 carbon atoms and one or both of said fatty acids is substituted at one to three carbon atoms with $C_{1-5}$-alkyl, and b) a second compound which is a bile acid salt or dihexanoyllecithin, wherein the concentration of the first compound in said composition is in the range from about 1 mg/ml to about 200 mg/ml and the molar ratio of the first compound to the second compound in said composition is in the range from 0.1:1 to 2:1.

24. The method of claim 23 wherein the first compound is a phosphatide in which two of the hydroxyl groups of the glycerol moiety of said phosphatide are esterified with said fatty acid residues, and said second compound is a bile acid salt.

25. The method of claim 24 wherein the concentration of said phosphatide is in the range from 10 mg/ml to 200 mg/ml, and the molar ratio of said phosphatide to said bile acid salt is in the range from 0.8:1 to 1.5:1.

26. The method of claim 25 which further comprises dissolving in said aqueous media a pharmaceutically active compound wherein said pharmaceutically active compound is present in said composition in a pharamaceutically effective concentration up to 50 mg/ml.

27. The method of of claim 26 wherein the fatty acid residues of said phosphatide are the same and have an odd number of carbon atoms in a straight chain.

28. The method of claim 27 wherein the fatty acid residues of said phosphatide are singly substituted by a methyl or ethyl group.

29. The method of claim 28 wherein the fatty acid residues of said phosphatide are substituted at carbon 8, 10 or 12 of said fatty acid residues.

30. The method of claim 29 wherein said phosphatide is 1,2-di(10-methylnonadecanoyl)-sn-glycero-3-phosphocholine, its enantiomers and its corresponding phosphoethanolamines.

31. The method of claim 30 wherein said phosphatide is 1,2-di(10-methylnonadecanoyl)-sn-glycero-3-phosphocholine.

32. The method of claim 31 wherein said bile acid salt is sodium glycocholate.

33. The method of claim 29 wherein said phosphatide is 1,2-di(10-methylstearoyl)-sn-glycero-3-phosphocholine, its enantiomers and its corresponding phosphoethanolamines.

34. The method of of claim 33 wherein said phosphatide is 1,2-di(10-methylstearoyl)-sn-glycero-3-phosphocholine.

35. The method of claim 34 wherein said bile acid salt is sodium glycocholate.

36. The method of claim 29 wherein said phosphatide is 1,2-di(8-methylheptadecanoyl)-sn-glycero-3-phosphocholine, its enantiomers and its corresponding phosphoethanolamines.

37. The method of claim 36 wherein said phosphatide is 1,2-di(8-methylheptadecanoyl)-sn-glycero-3-phosphocholine.

38. The method of claim 37 wherein said bile acid salt is sodium glycocholate.

39. The method of claim 29 wherein said phosphatide is 1,2-di(8-methylpalmitoyl)-sn-glycero-3-phosphocholine, its enantiomers and its corresponding phosphoethanolamines.

40. The method of claim 39 wherein said phosphatide is 1,2-di(8-methylpalmitoyl)-sn-glycero-3-phosphocholine.

41. The method of claim 40 wherein said bile acid salt is sodium glycocholate.

42. The method of claim 29 wherein said phosphatide is 1,2-di(10-ethylstearoyl)-sn-glycero-3-phosphocholine, its enantiomers and its corresponding phosphoethanolamines.

43. The method of claim 42 wherein said phosphatide is 1,2-di(10-ethylstearoyl)-sn-glycero-3-phosphocholine.

44. The method of claim 43 wherein said bile acid salt is sodium glycocholate.

* * * * *